US006632088B2

(12) United States Patent
Voudouris

(10) Patent No.: US 6,632,088 B2
(45) Date of Patent: Oct. 14, 2003

(54) POWERED ORTHODONTIC BRACKET

(75) Inventor: John C. Voudouris, Toronto (CA)

(73) Assignee: OrthoArm, Inc., Toronto (CA)

( * ) Notice: Subject to any disclaimer, the term of this patent is extended or adjusted under 35 U.S.C. 154(b) by 24 days.

(21) Appl. No.: 09/843,174

(22) Filed: Apr. 25, 2001

(65) Prior Publication Data

US 2003/0031975 A1 Feb. 13, 2003

(51) Int. Cl.⁷ ................................................. A61C 7/00
(52) U.S. Cl. ............................... 433/18; 433/8; 433/24
(58) Field of Search ............................. 433/2, 8, 9, 18, 433/24

(56) References Cited

U.S. PATENT DOCUMENTS

| | | | | |
|---|---|---|---|---|
| 3,353,271 A | * | 11/1967 | Blechman | |
| 3,654,702 A | * | 4/1972 | Kelly, Jr. | |
| 4,272,240 A | * | 6/1981 | Glassman | 433/18 |
| 4,519,779 A | * | 5/1985 | Lieb | 433/18 |
| 4,531,534 A | * | 7/1985 | Magill et al. | 137/75 |
| 4,712,999 A | * | 12/1987 | Rosenberg | 433/11 |
| 4,842,514 A | * | 6/1989 | Kesling | 433/21 |
| 5,760,692 A | * | 6/1998 | Block | 340/573 |

* cited by examiner

*Primary Examiner*—Ralph A. Lewis
(74) *Attorney, Agent, or Firm*—Michael Best & Friedrich LLP

(57) ABSTRACT

An orthodontic bracket assembly comprising an orthodontic bracket and a powered actuator mounted to the bracket. The actuator can be used to provide relative movement between a tooth (or set of teeth) and another object, such as an archwire or another tooth (or set of teeth). Preferably, the actuator is a micro electromechanical system (MEMS) having a size that will not significantly interfere with the comfort of the patient.

19 Claims, 1 Drawing Sheet

POWERED ORTHODONTIC BRACKET

FIELD OF THE INVENTION

This invention relates generally to the field of orthodontics and, more particularly, to orthodontic brackets.

BACKGROUND OF THE INVENTION

Orthodontic brackets typically are attached to individual teeth and connected to an archwire. This assembly is commonly used to move and straighten teeth. Teeth are moved and rotated by applying forces on the bracket. Typically, rubber bands or other resilient devices have been used to apply the desired forces. This requires many visits to the orthodontist to check and replace worn out rubber bands. Another device used to move and straighten teeth is headgear. Headgear is typically wrapped around the back of the wearer's head and attached to the teeth requiring movement. This can be uncomfortable and/or unattractive for the wearer. Both methods of moving and straightening teeth require many check-ups, which are costly and are a significant factor in the cost of orthodontic treatment.

SUMMARY OF THE INVENTION

The present invention alleviates one or more of the above-noted issues by providing an orthodontic bracket assembly that can move a tooth without the need for standard elastic components. More specifically, the present invention provides an orthodontic bracket assembly comprising an orthodontic bracket and a powered actuator mounted to the bracket. The actuator can be used to provide relative movement between a tooth (or set of teeth) and another object, such as an archwire or another tooth (or set of teeth). Preferably, the actuator is a micro electromechanical system (MEMS) having a size that will not significantly interfere with the comfort of the patient.

In one embodiment, the assembly includes a rotary MEMS that is mounted to the bracket and that includes a wheel. In this embodiment, the wheel is positioned to engage the archwire so that force applied by the MEMS will result in relative movement between the tooth and the archwire. Engagement between the actuator and the archwire can be by any suitable means, such as frictional engagement (e.g., using a rubber material) or mechanical engagement (e.g., using teeth or other engaging mechanism).

DETAILED DESCRIPTION

Figure 2:
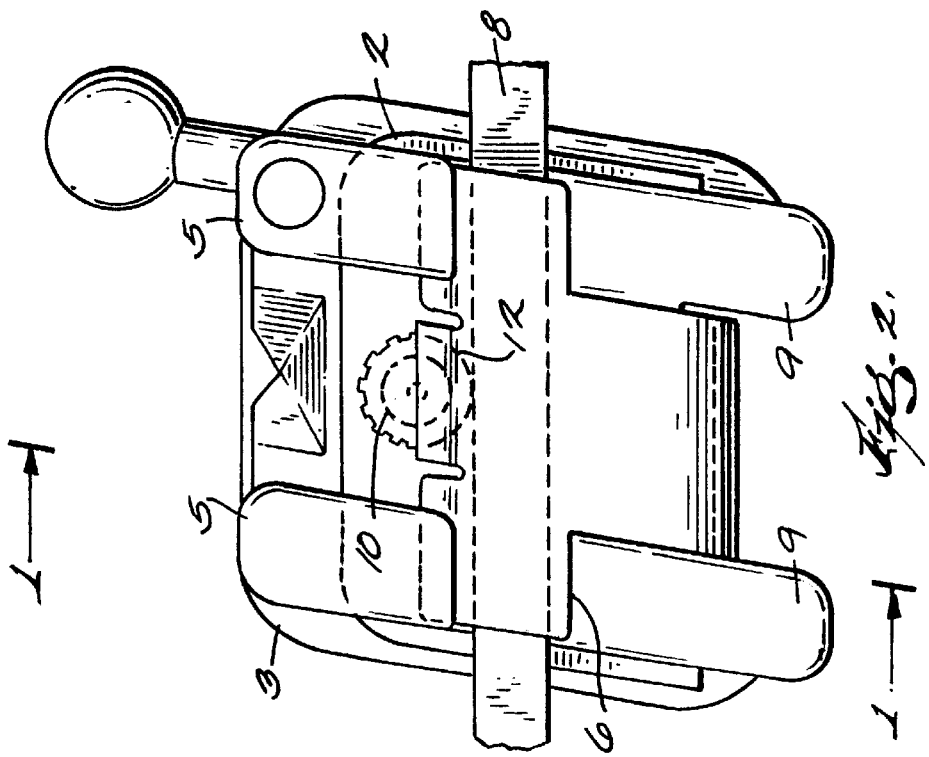
FIG. 2 is a front view of the bracket of FIG. 1
Figure 1:
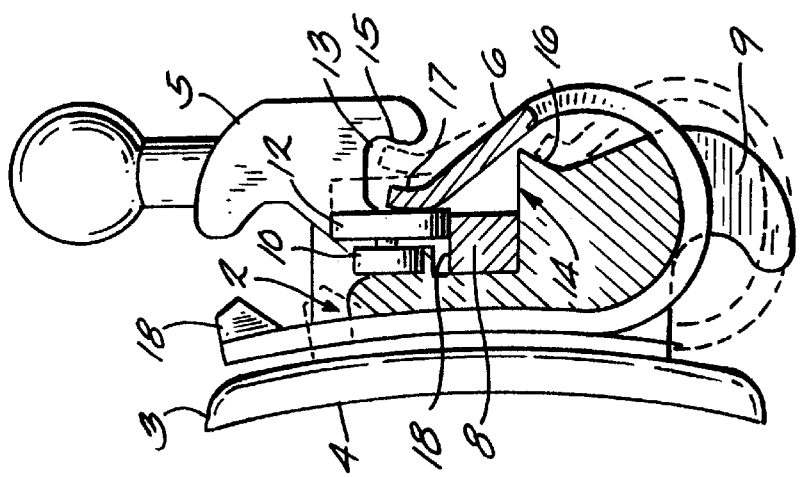
FIG. 1 is a side view of a bracket embodying the present invention

With reference to FIGS. 1 and 2, an orthodontic bracket assembly is illustrated according to the preferred embodiment for application to an upper tooth, although the same principles apply for brackets adapted for use with lower teeth. The bracket assembly includes a base 2, a sliding locking member 6 for securing an archwire 8 and an actuator.

The base 2 includes a lingual portion 3 for attachment to a tooth by means of a mounting pad 4 or other suitable means. A pair of gingival tie wings 5 and a pair of occlusal tie wings 9 extend from the base in a buccal-labial direction. An archwire slot 14 extends generally horizontally across the base 2 and opens for receiving the archwire 8.

The base 2 includes a groove 13 extending downward from the gingival tie wings 5. The groove 13 provides an operable locking surface 15 for the sliding locking member 6. According to the preferred embodiment, a second locking surface 16 is provided to lock the locking member 6 in an open position to allow removal and maintenance of the archwire 8.

According to the preferred embodiment, the sliding locking member 6 is generally in the shape of a "U". The locking member 6 curves at one end to form a generally hook-shaped catch 17 and at the opposite end a stopper 18 is attached for contacting the base 2, thereby preventing the locking member 6 from sliding off of the base 2 in the open position. The locking member 6 is movable from a closed position (shown in solid lines in FIGS. 1 and 2) to an open position (shown in broken lines in FIG. 1). The general operation of the bracket and locking member is disclosed in more detail in U.S. patent application Ser. No. 09/327,732, which is incorporated herein by reference in its entirety.

As shown in FIGS. 1 and 2, the actuator 10 is secured to the base 2. According to the preferred embodiment, the actuator 10 is a Microelectromechanical System (MEMS) with rotary capabilities. MEMS are powered by internal power mechanisms, the specifics of which are not the subject of the present invention. This embodiment is not meant to limit other types of actuators capable of achieving the same desired results, such as linear actuators capable of moving in lateral directions. The actuator 10 is coupled to a moving member in the form of a wheel 12, and the wheel 12 contacts the surface 18 of the archwire 8.

Figure 3:
FIG. 3 is a perspective view of a wheel coupled to a motor.

According to preferred embodiment shown in FIG. 3, the wheel 12 has the surface contacting the archwire 8 lined with a high friction material such as rubber 20, thus creating friction between the two surfaces. In an alternative embodiment shown in FIG. 2, the contacting surface of the wheel 12 could have teeth that inter-lock with teeth on the surface 18 of the archwire 8, or any other suitable arrangement whereby force can be transferred from the actuator to the archwire. The embodiments of the wheel 12 are not meant to be limiting and any suitable embodiments that achieve similar results can be used.

The actuator 10 is programmed to apply a constant or varying force to drive the wheel 12, wherein the wheel 12 rolls against the surface 18 of the arch wire 8. The friction that occurs between the surface of the wheel 12 and the surface 18 of the archwire 8 produces a force on the base 2 of the bracket, therefore producing a force on the tooth. The base 2 and the archwire 8 can be set up in many different orientations to exert the resulting force on the tooth in any desired direction. Alternatively, the actuator 10 could be programmed to move along the archwire at a constant or varying rate of speed.

Because the bracket 6 is self-ligating, the movement of the bracket will not be inhibited by elastic contacting the archwire 8. The motor 10 also alleviates the need for elastic chain placement used commonly from the back first molar to the upper front tooth such as a cuspid to close a space in the middle of an upper bicuspid extract.

In summary, motorized orthodontic brackets enjoy the advantages of a programmable actuator as well as the advantages of eliminating rubber bands. The programmable actuator is advantageous over current methods such as rubber bands because the actuator can be programmed to provide a constant force on a tooth, therefore having the ability to move teeth over long distances without the need for orthodontic inspections. Rubber bands also have a tendency to break and become discolored, thereby requiring many visits to the Orthodontist for replacement.

The foregoing description of the present invention has been presented for purposes of illustration and description; furthermore, the description is not intended to limit the invention to the form disclosed herein. Consequently, variations and modifications commensurate with the above teachings, and the skill or knowledge of the relevant art, are within the scope of the present invention. The embodiments described herein are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. An orthodontic bracket assembly comprising:
    an orthodontic bracket including a base having a lingual portion for attachment to a tooth; and
    an electromechanical actuator mounted to the bracket and including a moving member.
2. The orthodontic bracket assembly of claim 1, wherein the bracket further includes an archwire slot, and wherein the assembly further comprises a locking member coupled to the bracket and movable between an open position where access to the archwire slot is permitted and a closed position where access to the archwire slot is inhibited.
3. The orthodontic bracket assembly of claim 2, wherein the actuator comprises a rotary actuator.
4. The orthodontic bracket assembly of claim 3, wherein the rotary actuator comprises a wheel.
5. The orthodontic bracket assembly of claim 4, wherein the wheel includes a high friction material adapted to facilitate frictional engagement with the archwire.
6. The orthodontic bracket assembly of claim 4, wherein the wheel comprises teeth adapted to facilitate frictional engagement with the archwire.
7. The orthodontic bracket assembly of claim 1, wherein the bracket includes at least one tie wing.
8. The orthodontic bracket assembly of claim 1, wherein the actuator comprises micro electromechanical system.
9. An orthodontic bracket and archwire assembly comprising:
    an orthodontic bracket including a base having a lingual portion for attachment to a tooth, and further having an archwire slot;
    an archwire positioned in the slot; and
    a programmable actuator mounted to the bracket and including a moving member engaged with the archwire.
10. The orthdodontic bracket and archwire assembly of claim 9, further comprising a locking member coupled to the bracket and movable between an open position where access to the archwire slot is permitted and a closed position where access to the archwire slot is inhibited.
11. The orthodontic bracket and archwire assembly of claim 9, wherein the bracket includes at least one tie wing.
12. The orthodontic bracket and archwire assembly of claim 9, wherein the actuator comprises micro electromechanical system.
13. The orthodontic bracket and archwire assembly of claim 9, wherein the actuator comprises a rotary actuator.
14. The orthodontic bracket and archwire assembly of claim 13, wherein the rotary actuator comprises a wheel.
15. The orthodontic bracket and archwire assembly of claim 14, wherein the wheel includes a high friction material adapted to facilitate frictional engagement with the archwire.
16. The orthodontic bracket and archwire assembly of claim 14, wherein the wheel comprises teeth adapted to facilitate frictional engagement with the archwire.
17. A method of moving a tooth of a patient, comprising:
    attaching a bracket having an archwire slot to the tooth;
    inserting an archwire into the archwire slot;
    engaging a motorized actuator between the bracket and the archwire; and
    actuating the actuator to provide relative movement between the bracket and the archwire.
18. A method of moving a tooth as claimed in claim 17, wherein engaging comprises mounting the actuator to the bracket and engaging the actuator with the archwire.
19. A method of moving a tooth as claimed in claim 17, wherein the actuator comprises a rotary actuator and wherein actuating comprises rotating at least a portion of the actuator.

* * * * *